United States Patent [19]
Mason et al.

[11] Patent Number: 4,989,337
[45] Date of Patent: Feb. 5, 1991

[54] LEG MEASURING DEVICE

[76] Inventors: Jeffrey T. Mason, 2142 Beartrap, Escondido, Calif. 92027; Charles A. Bastyr, 12476 Rue Fountainbeau, San Diego, Calif. 92131; Bradley R. Mason, 1205 Caminito Carolina, Olivenhain, Calif. 92024

[21] Appl. No.: 308,259

[22] Filed: Feb. 8, 1989

[51] Int. Cl.⁵ .............................................. A61B 5/103
[52] U.S. Cl. ...................................... 33/512; 128/774; 33/511
[58] Field of Search ........................ 33/511, 512, 515; 128/80 C, 80 F, 774

[56] References Cited

U.S. PATENT DOCUMENTS

| 3,832,780 | 9/1974 | Lewis ...................................... 33/512 |
| 4,201,226 | 5/1980 | Phillips ................................... 33/512 |
| 4,834,057 | 5/1989 | McLeod, Jr. ........................... 33/512 |

FOREIGN PATENT DOCUMENTS

| 0142148 | 6/1980 | Fed. Rep. of Germany ...... 128/774 |
| 1090339 | 5/1985 | U.S.S.R. ............................... 128/774 |
| 1404058 | 6/1988 | U.S.S.R. ............................... 128/774 |
| 8804536 | 6/1988 | World Int. Prop. O. .......... 128/774 |

Primary Examiner—William A. Cuchlinski, Jr.
Assistant Examiner—Alvin Wirthlin
Attorney, Agent, or Firm—Harness, Dickey & Pierce

[57] ABSTRACT

A device for measuring a leg about the knee for the fitting of a knee brace. The device measuring the width of the knee about a lateral axis extending laterally across the knee abut the knee's condyles, the circumference of the upper leg and lower leg a predetermined distance from said lateral axis and the offset of the leg. Optionally, the contour of the front portion of the upper leg and rear portion of the lower leg at the predetermined distance is measured by the device.

19 Claims, 3 Drawing Sheets

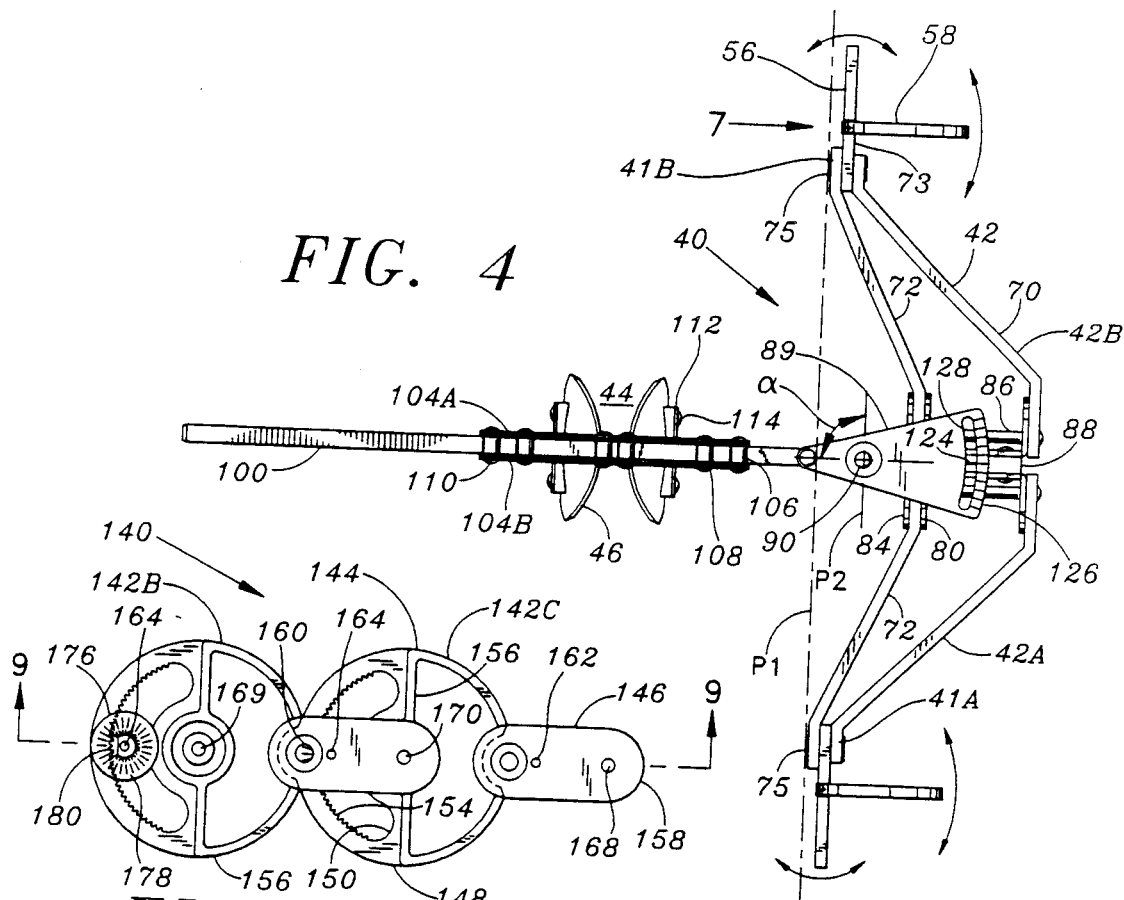
FIG. 4
FIG. 6
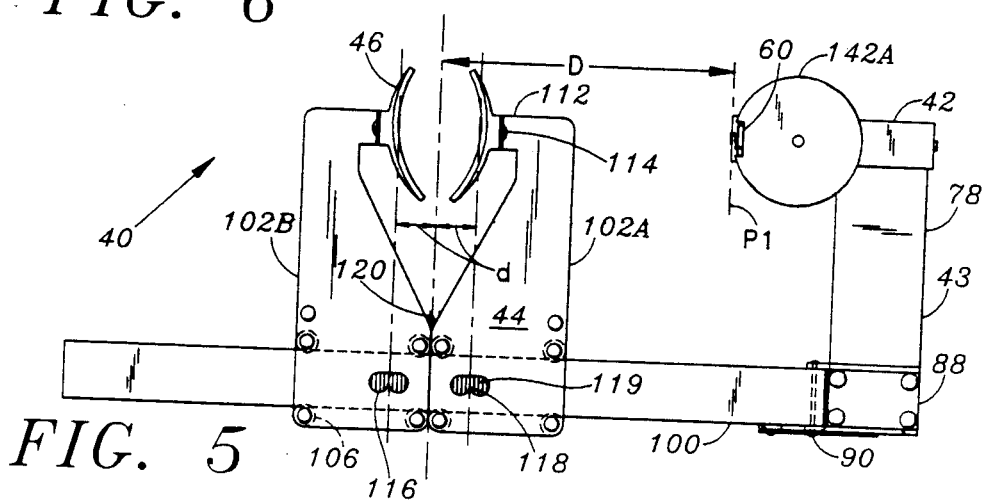
FIG. 5

LEG MEASURING DEVICE

BACKGROUND OF THE INVENTION

1. Field of the Invention

The present invention is directed to an orthopedic measuring device for the leg and it particularly relates to a device for measuring crucial dimensions and contours of the leg for the fitting of an orthopedic device such as a knee brace, leg brace and alike.

2. Description of the Prior Art

Many people wear leg braces, especially knee braces, to strengthen and/or stabilize the leg due to injuries to the leg, caused by athletic endeavors, surgical procedures, accidents, birth defects, disease and alike. Because of the nature of the injury, the wearer frequently must have a custom fit leg brace or knee brace to obtain the desired degree of strengthening and/or stabilization. At the present time, almost all the custom made leg braces and knee braces are fitted by taking measurements from, or fitting to, a plaster mold of the leg or knee. This is not always a successful method of fabricating or fitting a brace because the plaster mold can be accidentally crushed, or the mold can be inaccurate because of swelling to the leg, resulting from the injury, at the time the mold is made, or because there are no guidelines or reference points to indicate exactly what portion of the leg is represented by the plaster of Paris mold. Thus, unless the mold has been properly marked, which in most cases it is not, it can be extremely difficult to determine where the axis of rotation of the knee is from the mold. Frequently a custom brace made from such a plaster of Paris mold does not properly fit the intended wearer because the mold does not correctly represent the leg or the position of the mold with respect to the leg is not known. In those circumstances, a new mold of the leg has to be made and a new brace fabricated.

An object of the present invention is to provide an orthopedic device for taking measurements of the leg, including the knee, for the fabrication and/or fitting of braces for the leg, including the knee. Such a device could be utilized to make the necessary measurements for a fabrication and/or fitting of the knee and leg braces disclosed in U.S. Pat. Nos. 4,271,831; 4,481,941; 4,493,316; 4,531,515; 4,643,176 and 4,697,583.

It is an object of the present invention to provide a leg measuring device that can measure critical dimensions of the leg and critical shapes or contours of the leg needed for the fabrication and/or fitting of a leg brace. The terms "fitting" or "to fit" herein will be used to denote the fabrication and/or fitting of a leg brace.

Another object of the present invention is to provide a device that will yield standard measurements values which can be utilized to fit a custom made leg brace for the measured leg without the need of making a mold of the shape of the leg.

It is a further object of the present invention to provide a device that can measure the width of the knee about the condyles, the circumference of the lower leg about the calf region, the offset of the leg, the circumference of the upper leg about the mid thigh area, the contour of the anterior and/or posterior portion of the lower leg, the contour of the anterior and/or posterior portion of the upper leg, and/or, the angle between the axis of rotation, flexion and extension, of the leg and a reference line contacting the lateral side of the lower leg about the calf region and the lateral side of the upper leg in the region of the mid thigh. The offset of the leg is a measure of the spacial relationship of the condyles of the knee to the contact points of the leg measuring device on the upper and lower leg.

SUMMARY OF THE INVENTION

For purposes of describing the invention herein, the leg is described as having an X-axis, a Y1-axis and a Y2-axis. The X-axis extends from one side of the knee to the other side of the knee about the knee's condyles which are intersected by the axis of rotation of the knee. The Y1-axis extends vertically downward through the lower leg, from the midline of the knee and the Y2-axis extends vertically upward through the upper leg from the midline of the knee. Reference will also be made to X1 and X2 axis that are predetermined distances below and above the X-axis at specific points but not necessarily parallel to the X-axis. The X1-axis intersects the lateral side of the lower leg and the Y1-axis. The X2-axis intersects the lateral side of the upper leg and the Y2-axis. A line drawn from the point where the X1-axis intersects the lateral side of the lower leg to the point where the X2 axis intersects the lateral side of the upper leg is the reference line herein.

The orthopedic measuring device of the present invention comprises:

a. a caliper means adapted to be detachably attached to the medial and lateral sides of the knee about the X-axis;

b. support means adapted to be detachably attached to the lateral side of the upper leg above the knee and to the lateral side of the lower leg below the knee;

c. means for attaching the caliper means to the support means;

d. measurement means on said caliper means for measuring the width of the knee between the medial and lateral condyles about the X-axis; and e. measurement means on said caliper means for measuring the offset of the leg.

Preferably the device includes a means for pivotally attaching the caliper means on a horizontal axis that is perpendicular to the X-axis. Most preferably the device includes protractor means on the pivotally attaching means for measuring the angle between the X-axis and the support means.

Preferably the device includes a means on the support means for measuring the circumference of the upper leg at a predetermined distance above the X-axis and/or measuring the circumference of the lower leg at a predetermined distance below the X-axis. Preferably the device includes a scale means on the caliper means for measuring the width of the knee and the offset of the leg. The offset of the leg is a measure of the spatial relationship of the condyles to the lateral contact points of the device on the leg in the coronal plane.

In one embodiment of the invention the leg measuring device comprises:

a. a device adapted to measure a leg having an X-axis extending from one side of the knee to the other side about the knee's condyles, a Y1-axis extending vertically downward through the lower leg, through the midline of the knee, a Y2-axis extending vertically upward through the upper leg through the midline of the knee, and a reference line drawn from a first position on the lateral side of the upper leg a first predetermined distance above the X-axis to a second position on the lateral side of the lower leg a second predetermined distance below the X-axis;

b. a frame assembly having a front and a back end and a top side and a bottom side;

c. two half-bows each having a near end and a far end, the half-bows at their near end hinged to the frame assembly, each half-bow adapted to pivot independently on different parallel axes;

d. a rail perpendicularly mounted on the frame assembly;

e. two jaws movably mounted on the rail, each jaw mounting a condyle cup, the X-axis and the axis of the condyle cups being coaxial, the condyle cups adapted to engage the lateral and medial sides of the knee, each jaw having indicator means;

f. means for detachably attaching the far end of one half-bow to said first position on the lateral side of the upper leg and the far end of the other half-bow to said second position on the lateral side of the lower leg; and g. scale means to the rail and cooperating with said indicator means on said jaws for the measurement of the width between the lateral and medial sides of the knee about the X-axis and the offset of the leg.

Preferably the rail is pivotally mounted on the front end of said frame assembly and is adapted to pivot on a horizontal axis perpendicular to said X-axis. Most preferably, the device includes a protractor means cooperating with said rail and frame assembly and adapted to measure the angle between the X-axis and the reference line.

In a preferred embodiment, each half-bow is attached to the frame assembly by hinge means, each half-bow is adapted to pivot on an axis parallel to the X-axis.

Preferably the means for detachably attaching the far end of each half-bow to the leg comprises a strap means attached to the far end of the half-bow, the straps adapted to be wrapped completely around the leg and detachably attached thereto. In a preferred embodiment, the device includes measurement means to measure the circumference of the upper leg and lower legs commencing at the first position and second position respectively. The measurement means can comprise a tape measure having a linear scale attached to the far end of each half bow and adapted to be wrapped around the leg. Alternatively, the measurement means can comprise a tape measure having a linear scale attached to the outer surface of each strap and adapted to measure the outer circumference of the upper leg and lower leg when the strap means is wrapped around the leg. In one preferred embodiment of the invention, the device includes the means for measuring the contour of at least a portion of the leg; preferably the means for measuring the contour of the leg is mounted at the far end of a half-bow. In the most preferred embodiment of the present invention, the means for measuring the contour comprises a contour gauge which comprises:

a. a plurality of circular elements of a predetermined radius linked together in a hinge relationship on a common plane to form a chain, each circular element having an axis of rotation perpendicular to said common plane, each circular element spaced equal distance from its neighboring circular elements, said chain adapted to embrace the contour of a surface with each circular element contacting the surface;

b. hinge means to connect neighboring circular elements in a hinged relationship; and c. means on each circular element for determining the angle of each circular element with respect to the point of contact of each circular element with the surface and the next circular element in the chain.

Preferably the hinge means of the contour gauge comprises two parallel, spaced apart longitudinal tangs extending radially outward from the outer circumference of each circular element, the tangs embracing and pivotally attached to a neighboring circular element so that the neighboring circular element can pivot about its axis of rotation on said tangs.

Another embodiment of the present invention is directed to a method for measuring certain dimensions of a leg about the knee for a fitting of a knee brace to the leg, the leg having an X-axis extending from the lateral side of the knee to the medial side of the knee about the knee condyles, a Y1-axis extending vertically downward from the midline of the knee through the lower leg, a Y2-axis extending vertically upward from the midline of the knee through the upper leg, and a reference line from a first position on the lateral side of the upper leg a first predetermined distance about the X-axis to a second position on the lateral side of the lower leg a second predetermined distance below the X-axis, the method comprising:

a. measuring the width of the knee between the lateral and medial condyles; and b. measuring the angle between the X-axis and the reference line, or measuring the offset of the leg.

In a preferred embodiment of the method, the circumference of the upper leg at a third predetermined distance above the X-axis and/or circumference of the lower leg at a fourth predetermined distance below the X-axis is measured. Preferably the third predetermined distance is equal to the fourth predetermined distance. Most preferably, the first predetermined distance, the second predetermined distance, the third predetermined distance, and the fourth predetermined distance are equal. In another preferred embodiment of the present invention, the contour of at least a portion of the upper leg at a fifth predetermined distance above the X-axis is measured and/or the contour of the lower leg at a sixth predetermined distance below the X-axis is measured. Preferably the fifth predetermined distance and the sixth predetermined distance are equal. Most preferably, the first predetermined distance, the second predetermined distance, the fifth predetermined distance and the sixth predetermined distance are equal.

Another embodiment of the present invention is directed to a method of measuring the contour of the leg, the leg having an X-axis extending from the lateral side of the knee to the medial side of the knee about the knee condyles, a Y1-axis extending vertically downward from the midline of the knee through the lower leg, a Y2-axis extending vertically upward from the midline of the knee through the upper leg, and a reference line drawn from a first position on the lateral side of the upper leg a first predetermined distance above the X-axis to a second position on the lateral side of the lower leg a second predetermined distance below the X-axis, an XX-axis, e.g., axis X1 of FIGS. 1 and 2, spaced apart from the X-axis extending from the medial side of the leg to the lateral side of the leg intersecting said first position or second position, the method comprising:

a. establishing a plurality of reference points above the surface of a leg and on a plane parallel to the XX-axis;

b. establishing a plurality of corresponding tangent points on the surface, a straight line extending upwardly from each tangent point to the corresponding reference point being perpendicular to the tangent line to the surface drawn through the tangent point and lying in said plane, each reference point being equal distance from its neighboring reference points and its corresponding tangent point; and c. for each reference point, measuring the angle between the perpendicular line for such reference points and a straight line from such reference point to the next adjoining reference point, and/or for each reference point, measuring the angle between (i) the straight line from such reference point to the reference point of one of the two next adjoining reference points and (ii) the straight line through such reference point that is parallel to the corresponding tangent line for such reference point or the straight line from such reference point to the reference point of the other next adjoining reference point.

The contour of the surface can be plotted by utilizing the angle measurements, the known distance between the tangent points and the corresponding reference points and the known distance between the adjacent reference points.

If the contour of a surface is measured by employing the contour gauge of the present invention, the contour of the surface can be plotted or duplicated by manipulating a contour gauge or contour plotter having the same dimensions and angle scale as the measurement contour gauge so that the angle readings of each circular element of the plotting contour gauge tracks the angle readings of the measurement contour gauge employed to measure the surface.

If desired, a series of jigs or molds can be fabricated; each jig or mold of the series having a surface that is depicted by its own unique set of angle readings from the contour gauge. Thus the surface of one jig or mold might yield a set of angle readings with a contour gauge equivalent to 75°, 75°, 75°, 75°, 75° and 75° whereas the surface of the next jig or mold might yield a set of angle readings with a contour gauge equivalent to 74°, 76°, 75°, 75°, 75° and 75°. Preferably the circumference of the upper leg at a predetermined distance above the lateral and medial condyles is measured and/or the circumference of the lower leg at a predetermined distance below the lateral and medial condyles is measured. The circumference of the upper and lower legs are measured so that the restraining straps of a proper length can be fitted to the leg brace.

Preferably the contour of at least a portion of the upper leg, a predetermined distance above the lateral and medial condyles is measured and/or the contour of at least a portion of the lower leg at a predetermined distance below the lateral and medial condyles is measured. Most preferably, the contour of the anterior portion of the upper leg is measured and/or the posterior portion of the lower leg is measured. In the most preferred embodiment, the contour of the anterior portion of the middle thigh region of the upper leg is measured and the contour of the posterior portion of the calf region of the lower leg is measured. The contour of the upper leg and lower leg is measured to prepare and fabricate thigh cuffs and calf cuffs, for knee braces (See U.S. Pat. No. 4,697,583).

The cuffs are preferably contoured to the upper leg and lower leg to give a knee brace having the best fit which provides the maximum wearer comfort and the greatest strength and stability to the leg and knee. In many braces, a brace restraining strap is mounted on the brace opposite the cuff. However, in other instances, the strap may be situated between the cuff and the knee and/or several straps may be situated between the knee and the cuff to give maximum support to the leg via the brace. Accordingly, in some instances the circumference of the upper leg and/or the lower leg will be taken at several positions above and below the X-axis. In most instances the restraining straps on the upper leg and lower leg will be equal distance from the X-axis. However, in some instances the restraining straps on the upper leg and lower leg will be difference distances from the X-axis. In some instances, the cuffs for the upper leg and the lower leg will be equal distance from X-axis. However, in other instances the cuff for the upper leg will be a different distance from the X-axis than the cuff for the lower leg.

For proper fitting of a brace, that is for the proper fabrication of a customized brace or the proper selection of a ready made brace, the brace must "fit" the leg. Any set of measurements for an object must have at least one reference point that the measurements can relate back to. For the leg, the lateral and medial condyles offer an excellent set of reference points. The lateral and medial condyles protrude from the sides of the knee and reflect the lateral and medial condyles of the femur and the tibia at their lower end and upper end respectfully. The lateral and medial condyles can be quickly located by feel by extending the knee and/or flexing the knee. The condyles roughly represent the axis of rotation of the knee. The human knee is a very complex structure and it does not have a single axis of rotation. The "axis of rotation" of the knee moves as the knee is bent. When the leg is longitudinally extended, such as when standing up, the "axis of rotation" of the knee intersects the lateral and medial condyles of the knee. Herein the "axis of rotation" of the knee will be considered the axis of rotation when the leg is extended and will be the X-axis of the leg. Other X-axes of the leg will be identified herein with numbers, such as XX, X1, X2 and the like. These 'other' X-axes will be above or below the X-axis and may or may not be parallel to it.

To fit a customized brace or to fit a ready made brace, the width of the knee must be measured in order to fit a brace with condyle pads that engage the knee, or to fit a brace without condyle pads or similar components that is wide enough to clear the knee and not chap the knee when worn. In addition, since the lower leg and upper leg are not coaxial with respect to their Y-axes, it is important to measure the offset of the leg. The present device permits this offset to be measured and permits the fabrication of a custom brace or an optimum selection of a ready made brace to accommodate the particular leg geometry of the wearer. The fitting of a brace having the same geometry as the knee and upper and lower leg provides a brace that gives the wearer the most comfort and freedom of action, and the brace provides the wearer with greater leg strengthening and stabilization.

DESCRIPTION OF THE DRAWINGS

FIG. 4 is a front elevational view of the leg measuring device of the present invention;

FIG. 5 is a top plan view of the leg measuring device of the present invention;

FIG. 6 is a top plan view of a portion of the contour gauge of the leg measuring device of the present invention;

DETAILED DESCRIPTION OF THE INVENTION

Figure 1:
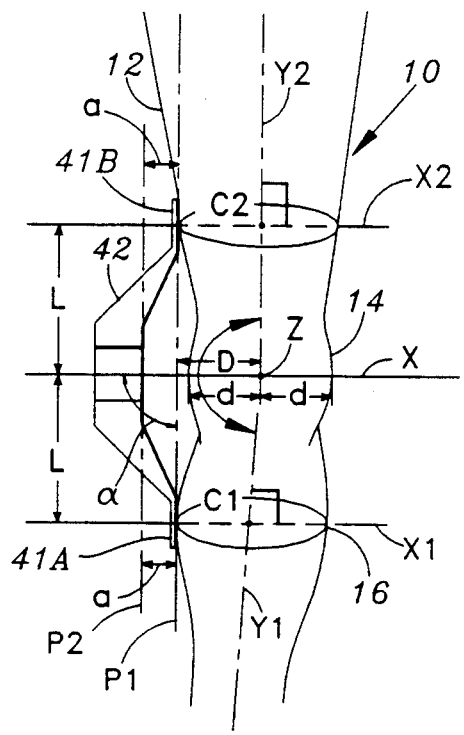
FIG. 1 is a front elevational view showing the upper leg and lower leg in the vicinity of the knee.

FIG. 1 illustrates some of the dimensions of the leg 10 that can be measured with the leg measuring device 40 (FIGS. 3, 4 and 5) of the present invention. Knee 14 is divided by the horizontal X axis. A longitudinal axis Y1 extends down into the lower leg 16 from the midline or midpoint Z of the knee. Longitudinal axis Y2 extends up from the midline of knee into the upper leg 12. The outer circumference C1 of the lower leg is measured about the calf region of the lower leg in a plane lying on X1 axis which is perpendicular to the Y1 axis. The outer circumference C2 of the upper leg is measured about the mid-thigh region in a plane lying on the X2-axis which is perpendicular to the Y2-axis. The X1 and X2 axes intersect the lateral side of the lower and upper legs respectively. The X1 and X2 axes are shown to be parallel to the X-axis of FIGS. 1 and 2. However, in many instances the X1 and X2 axes are not parallel to the X-axis or to each other. The X1 and X2 axes are perpendicular to the Y1 and Y2 axes respectively. The points where the X1 and X2 axes intersect the lateral side of the leg will be referred to as the "brace/leg contact points" herein. The distances between the X-axis and the X1 and X2 lines are designated as L. The line designated as P1 is the reference line. The reference line contacts the lateral sides of the upper and lower legs where the X2 and X1 axes, respectively, intersect the lateral sides of the leg. Line P2 is parallel to reference line P1 and spaced apart the known distance 'a' from P1. The angle alpha between the X-axis and the P2 line is the same as the angle between the X-axis and the reference line P1.

The offset is the difference between the distance "d" (the half-width of the knee) and the distance "D" the distance between the midpoint or midline Z of the knee and the reference line P1 along the X-axis. This is a very useful measurement for the fitting of a brace because it defines the spacial relationship of the knee with respect to the brace/leg contact points. Another way to look at the offset is as the distance between the reference line and the lateral condyle of the knee.

The outer circumference C1 and C2 of the lower leg and upper leg respectfully can be measured with the device of the present invention. In addition the width 2d of the knee between the medial condyle and the lateral condyle on the X-axis can be measured with the device. For reference purposes the bow 42 of the leg measuring device 40 of the present invention is illustrated in FIG. 1. The far ends 41A and 41B of the bow are on reference line P1 and contact the lower leg and upper leg respectfully at the brace/leg contact points.

Figure 2:
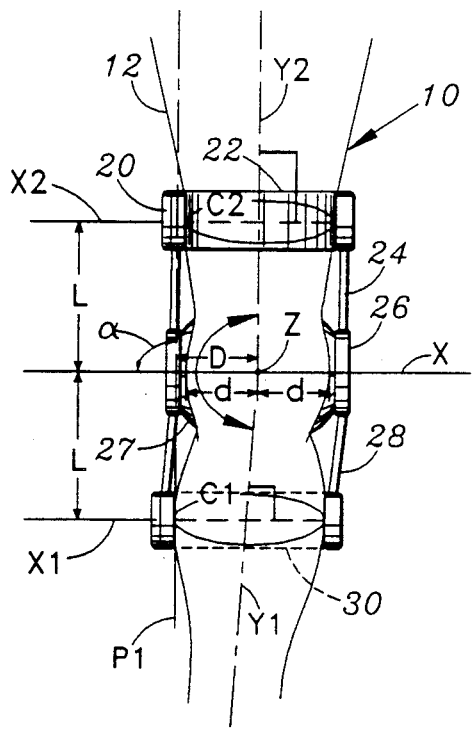
FIG. 2 is a front elevational view of the leg of FIG. 1 fitted with a knee brace.

FIG. 2 shows a leg 10 fitted with a knee brace having the dimensions described in FIG. 1. The lateral side of the leg in both FIGS. 1 and 2 is on the left side. The knee brace or articulating knee stabilizer 20 has an anterior thigh cuff 22 which is a rigid arcuate piece contoured to fit the front of the upper leg 12 in the region of the mid-thigh. The thigh cuff is connected to bicentric hinges 26 by femoral side bars 24. There is a side bar on the medial side and a side bar on the lateral side. The bicentric hinge is connected to a posterior calf cuff 30 by tibial side bars 28 on the medial side and the lateral side of the leg. The posterior calf cuff is a rigid arcuate piece contoured to fit the backside of the lower leg about the calf (not shown) region. The knee brace is attached to the upper leg by a restraining strap which goes behind the upper leg opposite the cuff and attaches to the cuff. The brace is attached to the lower leg by a strap that goes in front of the lower leg opposite the cuff and attaches to the cuff. The details regarding the fitting of knee braces are set forth in the patents described above, such as U.S. Pat. No. 4,697,583 which is directed to an anterior cruciate ligament brace. In that particular patent, the restraining straps of the brace are not illustrated as positioned on the leg opposite the cuffs; the straps are positioned near the bicentric hinge. The straps can be situated opposite the cuffs.

The brace is first fitted to the leg by fitting the condyle pads 27, attached to the inner sides of the hinges 26, to the medial and lateral condyles of the knee. In a preferred knee brace, the thigh cuff and calf cuff will both be shaped to fit the contour of the anterior mid-thigh and posterior calf regions. The cuff and straps will be fitted to meet the circumferences C1 and C2 of the lower leg and upper leg. The straps can wrap around the entire leg and over the cuffs. The lower cuff will intersect the X1 axis and the upper cuff will intersect the X2 axis. The center of the bicentric hinge will intersect the X axis. The X1 and X2 axes are shown to be equal distance from the X axis but braces can be constructed where the distances of X1 and X2 axes from the X-axis are not equal.

A knee brace which is custom fitted and incorporates the proper dimensions and contours of the leg, can be made to be stronger than 'off the shelf' braces.

Figure 3:
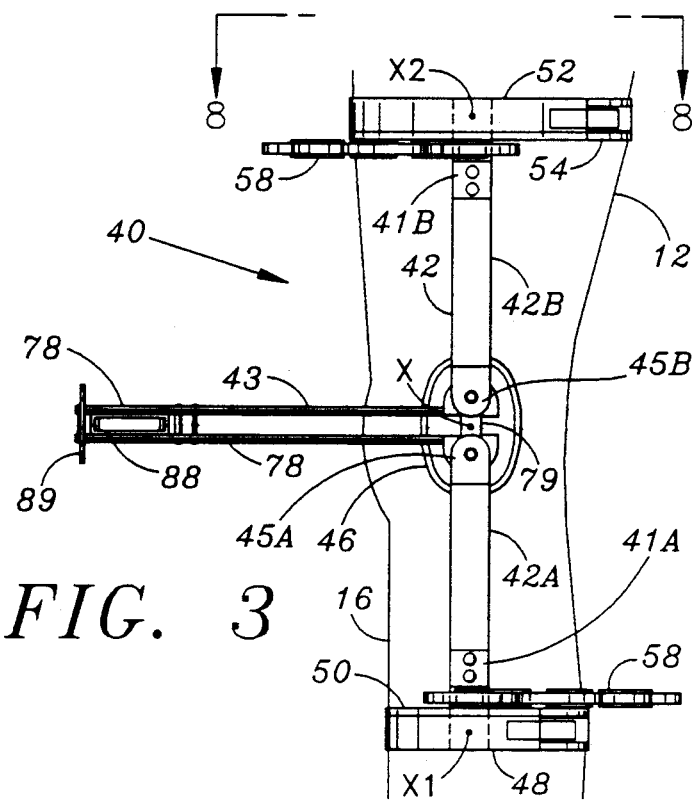
FIG. 3 is a side elevational view of a leg fitted with the leg measuring device of the present invention.

Referring to FIG. 3, the leg measuring device 40 of the present invention comprises the bow 42 (which is actually two half-bows 42A and 42B) which is connected to the lower leg 16 by lower attachment strap 48 and to the upper leg 12 by upper attachment strap 52. The lower attachment strap has a tape measure 50 attached thereto on one edge. The upper attachment strap also has a tape measure 54 attached to one edge. The tape measure has a linear scale either in metric or in English system which permits the measurement of the external circumference of the leg about the middle thigh and about the calf regions at a known distance L (see FIG. 1) from the X axis. The near ends 45A and 45B of the half-bows are hinged to frame assembly 43. Contour gauges 58 are attached to the far ends 41A and 41B of the bow to measure the contour of the anterior portion of the mid-thigh and the posterior portion of the calf.

Referring to FIGS. 4 and 5, each half-bow 42A and 42B comprises an outer rib 70 and inner rib 72. Arms 73 are attached to the far ends 41B and 41A of the half-bows and extend vertically upwardly and downwardly therefrom. The arms are positioned between the outer and inner ribs and are riveted to the ribs for structural strength and integrity, the interfaces of the half-bows 41a and 41b are designated as 75. The near ends 45A and 45B of the half-bows are hinged to frame assembly 43. Frame assembly 43 has upper and a lower spaced apart plates 78 (See FIG. 3) which are secured to a spacer 79 on their back ends and to base 88 at their front ends to form a rigid box frame assembly. The frame assembly at its back end on its top and bottom sides has channel braces 80 which together with the outer ribs 70, inner ribs 72, shafts 86 and plate 84 form hinge assemblies which permit the half-bows to pivot about shafts 86. The longitudinal axes of the shafts are parallel to the X-axis and are coaxial with the axes of rotation of the bicentric hinge of a brace. Preferably the half-bows can pivot on the hinge assemblies through an arc of about 20 of flextion from full extension (both half-bows in a straight line). The near ends of the half-bows, the channel braces and plate are apertured to receive the shafts. The hinge motion of the half-bows is substantially identical to the hinge motion of a bicentric hinge on the knee brace.

A rail 100 is pivotally attached to the front of the frame assembly 43 on pivot shaft 90. Rail 100 is adapted to receive arms 102A and 102B of the knee caliper 44. Each arm has an upper plate 104A and a spaced apart lower plate 104B with the rail running between the two plates. The arms ride on wheels 106, mounted on axes 110, which have outer flanges 108 which engage the top and bottom of the rail 100. Two arms are biased towards each other by return spring 120. The top plate and the bottom plate 102A and 102B of each arm have a window 116 with an indicator marker 118. These windows are superimposed over linear scales 116 on the top and bottom of rail 100. At the back end of each arm, ears 112 extend outwardly at right angles from each plate for receiving condyle cups 46. The condyle cups are riveted to the ears by rivets 114. When the knee calipers have been fitted to the knee with the condyle cups 46 engaging either side of the medial and lateral condyles of the knee, the width of the knee (dimension 2d, see FIG. 2) can be determined and the offset of the leg (the difference in d and D) can be determined. For example, if the linear scale is in centimeters and commences at plane P1, and if the measurement taken with arm 102A is 2.0 centimeters and the dimension taken with arm 102B is 14.0 centimeters, the width of the knee is 12.0 centimeters, the midpoint of the knee is 8.0 centimeters from P1 and the offset is 2.0 centimeters to the lateral side of the knee.

The knee caliper 44 can pivot with respect to the frame assembly 43 because rail 100 is pivotally attached to frame assembly 43 by shaft 90. A protractor plate 89 is secured to the front of rail 100 and has a scale 126 mounted thereon to measure angle (equivalent to angle alpha) between reference line P1 and the X-axis. The protractor plate has a window 128 adjacent the protractor scale which gives visual access to the indicator line (124) on the front of base 88 of the frame assembly.

Figure 7:
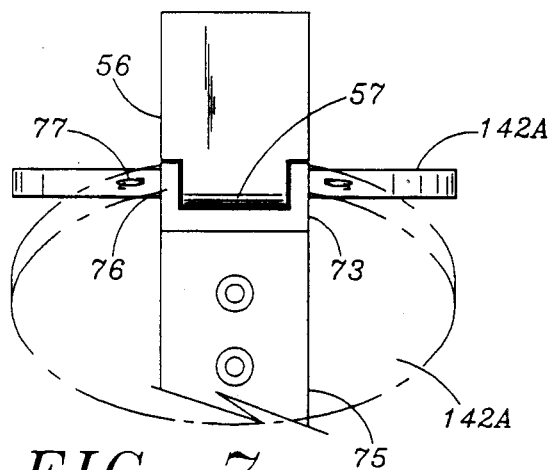
FIG. 7 is a enlarged view of a section of the leg measuring device of FIG. 4 from the direction of arrow 7.

Referring to FIG. 7 which is an enlargement of a portion of FIG. 4, the end of the arm 73 has ears 76. The space between the ears is adapted to receive the male portion 57 of the strap bracket 56. The outer side of arm 73 is adapted to receive the first circular element 142A of the contour gauge 140. A channel 60 (see FIG. 5) is cut peripherally into the first element 142A. The outer sides of ears 76 are adapted to receive the channel 60 of the first circular element in a hinge relationship. The hinge pin 77 extends through the first element into channel 60, into the left ear 76, through the male portion 57, through the right ear 76 and into the first element on the other side of the channel 60. The strap bracket 56 is hinged to the arm 73 to ensure that the strap fits the surface of the leg. The structure of the strap bracket, and the contour gauge is identical at both ends of the bow so that the leg measuring device can be put on either leg to take leg measurements. In fact the leg measuring device is suited so that it can be moved from the right to the left leg and vice versa by rotating the device about an axis extending perpendicularly from the plane of the paper of FIG. 4.

Each arm 102A and 102B of the knee caliper (FIG. 5) has windows 116 on both sides to read the scales 119 on both sides of the arm. The contour gauge (described below) has windows on both sides to read the circular scales on both sides. The straps on the far ends of the half-bows each have tape measures. Thus the device can be used to measure either leg.

The first circular element 142A of the contour gauge is also adapted to be rotated on a hinge pin 77 (FIG. 7) so that the contour gauge can be aligned on the surface of the leg.

Figure 9:
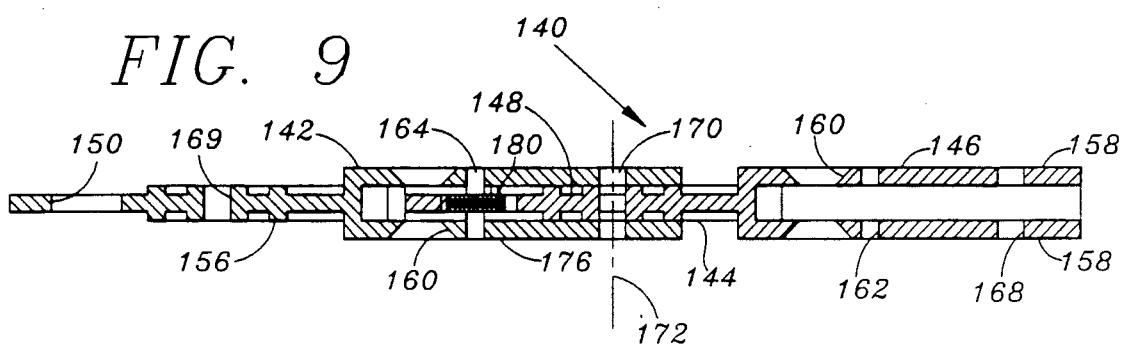
FIG. 9 is a side elevational view of the contour gauge of FIG. 6 from the direction of arrow 9.

The contour gauge 140 is shown in FIGS. 6 and 9. The contour gauge 140 comprises a plurality of circular elements 142A, 142B, etc. having a circular head portion 144 and a tongue portion 146. The circular head portion comprises a circular plate 148 having a raceway 150 which extends through the thickness of the plate and thus is open from both sides of the circular plate and partially extends around the plate. The outer wall of the raceway has a gear rack 154 adapted to cooperate with a gear wheel 180. The circular plate has a rib 156 which extends diagonally across the plate and around the back peripherally of the plate. The tongue portion 146 has two tangs 158 (see FIG. 9). Both tangs have windows 160, a wheel gear aperture 162 and a hinge aperture 168. The next adjoining circular element 142B to element 142A is adapted to rotate between the tangs of element 142A on the hinge shaft 170 about the axis of rotation 172 extending through the hinge aperture 168 of each tang and through the aperture 169 of the circular plate. The gear wheel 180 is positioned in the raceway in operative relation with the gear rack 154. The gear wheel is maintained in the raceway engaging the gear rack by shaft 164 riding in wheel gear aperture 162 of each tang. One each side of the gear wheel circular face plates 176 are mounted. Each circular face plate has a circular scale 178. The scale 178 is visible through the windows 160 in the top or bottom tangs. Each circular element is adapted to rotate on shaft 170 between the tangs 1568 of the tongue portion 146 of the adjoining circular element. As the circular element is rotated about shaft 170, gear wheel 180, which is in operative engagement with gear rack 154, turns causing the face plate 176 to turn. The circular scale on the circular face plate visible through window 160 designates a given value for the degree of rotation of the circular element. In the device illustrated in FIG. 6, the scale is marked off with alphabetical letters. The scales could also be marked off with arbitrary numeral values, degree values, or the like.

Figure 8:
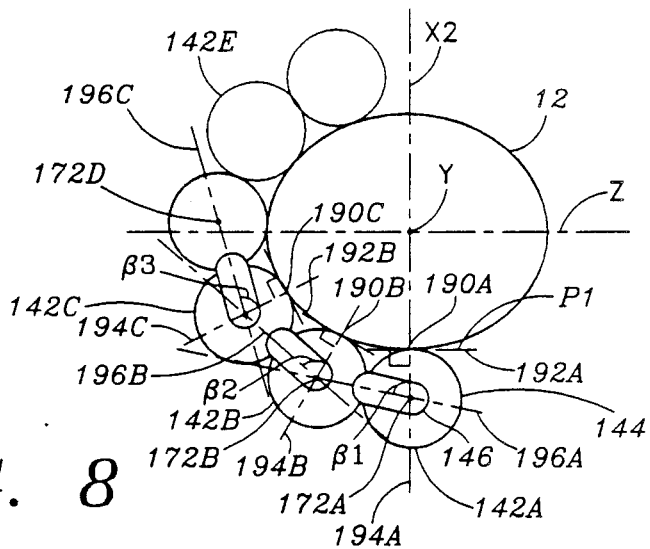
FIG. 8 is a top plan view along lines 8—8 of FIG. 3 of the contour gauge of the leg measuring device of the present invention.

Use of the contour gauge in 140 is illustrated in FIG. 8. FIG. 8 is taken along lines 8—8 of FIG. 3 and shows the contour gauge being utilized on the anterior portion of the upper leg about the mid-thigh region. The first circular element 142A of the contour gauge coincides with the axis X2 and is tangent to the P1 plane. Each circular element 142 is free to rotate with respect to its adjoining circular elements. Thus the contour gauge can be bent or wrapped around the leg surface in a common plane to follow the contour of the anterior portion of the leg. Each circular element makes contact with the leg at a point 190A, 190B, etc. A line 194A, 194B, etc. drawn from the axis of rotation 172A, 172B, etc. of a circular element to the point of contact on the leg (perpendicular line) is perpendicular to the tangent line 192A, 192B, etc. at the point of contact. The angle beta between the perpendicular line 194A, 194B, etc. of a circular element and a line 196A, 196B, etc. drawn from the axis of rotation of such circular element and the next adjoining circular element is indicated on the circular scale 180 of such element.

The radius of each circular element is identical, this radius is known, the distance between each element is known (2 radii), and the commencement point of the contour gauge on axis X2 is known. By employing these known dimensions and the beta angles for each circular element, the contour of the leg can be easily plotted. The contour gauge can be made with two or more circular elements. We have found that with circular elements having a radius of about 2 inches, a contour gauge of six linking circular elements can measure the contour of the anterior or posterior regions of the leg. Although the contour gauges of the present device have been positioned to measure the anterior region of the upper leg and the anterior region of the lower leg, the contour gauges can be positioned on the leg measuring device to measure the posterior portion of the upper leg and/or the anterior portion of the lower leg. In addition, the device can be fabricated with two or more contour gauges to develop a three dimensional contour of a region of the leg. For example, if a relatively long cuff is to be used on a brace, such as a cuff 6 to 8 inches in height, the leg measuring device can be modified with an arm 73 adapted to support 2 or more contour gauges.

The leg measuring device of the present invention is utilized by first placing the condyle cups 46 of the leg calipers on the medial condyle and lateral condyle of the knee. After the leg calipers are in place on the knee, the upper restraining strap 52 (FIG. 3) and the lower restraining strap 48 (FIG. 3) are wrapped around the leg to secure the bow to the upper and lower legs as described above. The restraining straps have measuring tapes 50 and 54 to measure the circumference of the leg. The leg can be measured in the English system, the metric system, or any other system which is suitable. The restraining strap can be secured by Velcro brand strips so the straps can be easily attached and detached. The knee and offset measurements from the knee caliper are taken and the alpha angle is taken from the protractor 89. The counter gauges are wrapped around the anterior of the upper leg and the posterior of the lower leg, and the beta angle measurements are taken on the contour gauge.

Rather than measuring the beta angle to determine or plot the contour of a surface, the angle between the two straight lines of a circular element that extend from the axis of rotation of such circular element to the axes of rotation of its two adjoining circular elements, such as the angle between lines 196B and 196C, can be used to determine the counter of a surface. To find such an angle for the first circular element 142A, the angle would be between line 196A and a line parallel to the tangent line 192A that intersects the axis of rotation 172A of the element.

The beta angle measurements are used to plot the contour of the anterior surface of the upper leg and the posterior surface of the lower leg to fabricate a custom contoured cuff for the upper leg and lower leg. The distance between the X axis and the X1 axis and X2 axis are known. Employing the measured distance between the condyles of the knee, utilizing the offset measurements, the using the angle alpha, a knee brace (bicentric hinges) can be fabricated that properly fits the wearer, such as the knee brace shown in FIG. 2. Alternatively the contour of a surface can be plotted with another contour gauge or contour plotter having the same dimensions and beta angle scale as the measurement contour gauge. In another embodiment, jigs or molds can be made with surfaces duplicating the measured surface so that a custom fit cuff can be made to fit the measured surface. The length of the brace restraining straps can be determined from the legs circumference measurements.

Although the device of the present invention has been shown with bicentric hinge elements, the device can also be made with single hinge elements for the manufacture of single hinge element knee braces, or with polycentric hinge elements for the manufacture of polycentric hinge element knee braces. In addition, the device can incorporate 3 or more tape measures to the measure the leg circumference at 3 or more positions to fit a brace with 3 or more restraining straps.

Moreover the device can be fabricated to measure the circumference of the leg and/or the contour of the leg from the upper thigh region down to the ankle.

What is claimed is:

1. A device for measuring a leg about the knee for the fitting of a knee brace comprising:
   a. a caliper means adapted to be detachably attached to the medial and lateral sides of the knee about the knee's X-axis which extends from one side of the knee to the other side of the knee about the knee's condyles;
   b. support means adapted to be detachably attached to the lateral side of the upper leg above the knee and to the lateral side of the lower leg below the knee;
   c. means for pivotally attaching the caliper means to the support means on a horizontal axis perpendicular to the X-axis;
   d. measurement means on said caliper means for measuring the width of the knee about the X-axis;
   e. second measurement means on said caliper means for measuring the offset of the leg; and
   f. means on the support means for measuring the external contour of at least a portion of the leg at a predetermined distance from the X-axis.

2. The device according to claim 1 including means on the support means for measuring the circumference of the upper leg at a predetermined distance above the X-axis.

3. The device according to claim 1 including means on the support means for measuring the circumference of the lower leg at a position that is a predetermined distance below of the X-axis.

4. The device according to claim 1 wherein said means on the support means for measuring the external contour of at least a portion of the leg is at a predetermined distance above the X-axis.

5. The device according to claim 1 wherein said means on the support means for measuring the external contour of at least a portion of the leg is at a predetermined distance below the X-axis.

6. The device according to claim 1 including means for measuring the angle between the X-axis and a reference line drawn from a point where the support means is attached to the lateral side of the upper leg to a point where the support means is attached to the lateral side of the lower leg.

7. A device for measuring the leg about the knee for the fitting of a knee brace to the leg comprising:
   a. a device adapted to measure a leg having an X-axis extending from one side of the knee to the other side about the knee's condyles, a Y1-axis extending vertically downward through the lower leg, from the midline of the knee, a Y2-axis extending vertically upward through the upper leg from the midline of the knee, a reference line drawn from a first position on the lateral side of the upper leg a first predetermined distance above the X-axis to a second position on the lateral side of the lower leg a second predetermined distance below the X-axis;
   b. a frame assembly;
   c. two half-bows each having a near and a far end, each half-bow at its near end attached to the frame assembly;
   d. a rail perpendicularly mounted on the frame assembly, the rail having top and bottom sides with longitudinal scales;
   e. two jaws movably mounted on the rail, each mounting a condyle cup, the X-axis and the axis of the condyle cups being coaxial, the condyle cup of one jaw adapted to engage the lateral side of the knee and the other condyle cup adapted to engage the medial side of the knee, each jaw having indicator means;
   f. means for detachably attaching the far end of one half-bow to said first position on the lateral side of the upper leg and the far end of the other half-bow to said second position on the lateral side of the lower leg; and
   g. scale means attached to the rail and cooperating with said indicator means for the measurement of the width between the lateral and medial sides of the knee about the X-axis and the offset of the leg.

8. The device according to claim 7 wherein the rail is pivotally mounted on the front end of said frame assembly and is adapted to pivot on a horizontal axis perpendicular to said X-axis.

9. The device according to claim 9 including a protractor means cooperating with said rail and frame assembly and adapted to measure the angle between the X-axis and the reference line.

10. The device according to claim 8 wherein the means for detachably attaching the far end of the half-bows to the leg comprises strap means attached to the far end of the half-bows, the straps adapted to be wrapped completely around the leg and detachably attached thereto.

11. The device according to claim 10 including a measurement means to measure the circumference of the upper leg and the lower legs commencing at the first position and the second position respectively.

12. The device according to claim 11 wherein the measurement means comprises a tape measure having a linear scale attached to a far end of each half-bow and adapted to be wrapped around the leg.

13. The device according to claim 12 wherein the measurement means comprises a tape measure having a linear scale attached to the outer surface of each strap means and adapted to measure the outer circumference of the upper leg and lower leg respectively.

14. The device according to claim 8 including a means for measuring the contour of at least a portion of the leg.

15. The device according to claim 14 wherein the means for measuring the contour of the leg is mounted at the far end of at least one of said half-bows.

16. The device according to claim 8 wherein each half-bow is attached to the frame assembly by hinge means, and each half-bow is adapted to pivot on an axis parallel to the X-axis.

17. The device according to claim 15 wherein the means for measuring a contour comprises a contour gauge which comprises:
   a. a plurality of generally planar circular elements of a predetermined radius having top and bottom sides linked together in a hinged relationship on a common plane to form a chain, each circular element having an axis of rotation perpendicular to said common plane, each circular element spaced an equal distance from its neighboring circular elements, said chain adapted to embrace the contour of a surface with each circular element contacting the surface;
   b. hinge means to connect neighboring circular elements in a hinged relationship so that a circular element rotates about the next circular element in a hinged relationship about the axis of rotation of the next circular element; and
   c. means on each circular element for determining the angle of each circular element with respect to the point of contact of such circular element with the surface and the next circular element in the chain.

18. The device according to claim 17 wherein said hinge means comprises two parallel, spaced apart longitudinal tangs extending radially outwardly from the outer circumference of each circular element, the tangs embracing the top and bottom sides of the next circular element wherein the outer ends of the tangs are pivotally attached at the axis of rotation of the next circular element so that a circular element can pivot about the axis of rotation of the next circular element in a hinged relationship.

19. The device according to claim 18 wherein the means on each circular element for determining the angle of each circular element comprises:
   a. each circular element having a circular raceway extending through from the top side to the bottom side and partially around the circular element, one wall of the raceway having a gear track;
   b. a gear wheel adapted to move in said raceway and operatively engaging said gear track;
   c. a circular face plate mounted on the side of the gear wheel above the raceway, the circular face plate hearing a circular scale;
   d. a gear shaft on which the gear wheel and circular face plate is mounted for rotation; and
   e. the tangs of each circular element having an aperture to receive for rotation the gear shaft of the next circular element and a window overlying the circular scale of the face plate on said gear shaft in order to determine the angle of said circular element.

* * * * *